United States Patent [19]

Johannesson

[11] Patent Number: 4,885,049
[45] Date of Patent: Dec. 5, 1989

[54] METHOD OF MANUFACTURE OF AN EXTERNAL CATHETER FOR MALE URINARY INCONTINENCE

[75] Inventor: Niels O. Johannesson, Espergerde, Denmark

[73] Assignee: Coloplast A/S, Denmark

[21] Appl. No.: 113,258

[22] Filed: Oct. 26, 1987

Related U.S. Application Data

[63] Continuation-in-part of Ser. No. 851,136, filed as PCT DK85/00068 on Jul. 12, 1985, published as WO86/00816 on Feb. 13, 1986, abandoned.

[30] Foreign Application Priority Data

Jul. 23, 1984 [DK] Denmark .................... 3598/84

[51] Int. Cl.$^4$ ................................ A61F 5/44
[52] U.S. Cl. ..................... 156/289; 156/294; 156/423; 604/352; 604/349
[58] Field of Search .......... 604/349, 351, 352; 128/138 R; 156/189, 289, 287, 294, 423, 285; 264/300, 301, 215; 428/36

[56] References Cited

U.S. PATENT DOCUMENTS

| | | | |
|---|---|---|---|
| 2,389,831 | 11/1945 | Welsh | 604/352 X |
| 2,568,128 | 9/1951 | Morris | 264/301 X |
| 2,604,092 | 7/1952 | Brown et al. | 604/352 X |
| 3,788,324 | 1/1974 | Lim . | |
| 3,863,638 | 2/1975 | Rogers, III et al. | 604/352 |
| 3,951,141 | 4/1976 | Kopelowicz . | |
| 4,013,494 | 3/1977 | Patterson | 156/294 X |
| 4,475,910 | 10/1984 | Conway et al. . | |
| 4,576,156 | 3/1986 | Dyck et al. | 128/138 R |

OTHER PUBLICATIONS

Mentor Corporation sales pamphlet entitled "New URO-SAN PLUS Male External Catheter", 4/19/1982.

*Primary Examiner*—David Simmons
*Assistant Examiner*—Jeff H. Aftergut
*Attorney, Agent, or Firm*—Ostrolenk, Faber, Gerb & Soffen

[57] ABSTRACT

A method for producing an external catheter for incontinence. The catheter has a hollow body section with an open end, and a second end which narrows into a discharge tube for the discharge of urine. The body section has an adhesive strip disposed on the inside of the body section and a covering layer disposed at a corresponding location on the outside of the body. Prior to use, the body section is rolled, and the adhesive layer contacts the cover layer, thus protecting the body section. The catheter may be prepared by arranging a prefabricated body portion around a mandrel which has previously been provided with a pressure sensitive adhesive.

8 Claims, 3 Drawing Sheets

METHOD OF MANUFACTURE OF AN EXTERNAL CATHETER FOR MALE URINARY INCONTINENCE

BACKGROUND OF THE INVENTION

1. Field of the Invention

This application is a continuation-in-part of U.S. application Ser. No. 851,136, filed as PCT DK85/00068 on Jul. 12, 1985, published as WO86/00816 on Feb. 13, 1986, now abandoned.

The invention relates to an external catheter for male urinary incontinence. More specifically, the catheter comprises a soft, thin-walled, substantially cylindrical body portion which is open at one end and merges at the other end into a narrowed drainage tube portion to be connected with a collecting bag. The body portion being provided on its inside with an adhesive. The catheter is manufactured in accordance with the process set forth herein using a specially designed mandrel.

2. Description of the Related Art

Catheters of this kind are designed to be arranged as a condom on a penis in order to act as an aid against male incontinence in a safe manner free of leakage and with the fewest possible inconveniences to the users, who may be physically handicapped or elderly persons for whom greater openness concerning problems of incontinence has led to a growing demand for such aids.

In order to securely fasten the catheter various accessories can be used in the form, inter alia, of separate adhesive tapes, as known for U.S. Pat. No. 3,520,305, or adhesive linings wound around or attached to the penis prior to arrangement of the catheter as known from U.S. Pat. No. 4,187,851. Also, compressible hydrophilic or hydrophobic lining members are known from GB published patent specification No. 2,096,901.

U.S. Pat. No. 3,788,324 discloses a catheter of the above mentioned kind. This catheter has an adhesive on its inside, thereby eliminating the use of special fastening means. Due to the adhesive, this catheter is delivered in an unfolded condition, and in order to facilitate the arrangement it is slotted almost on the total length of the body portion. During the manufacture, the catheter must be turned inside out in respect of the application of adhesive, and it must therefore be turned outside in to use, which may damage the catheter. Due to the slotting, a gel-like adhesive is required capable of providing tightening against leakage of urine backwards from the end at the drainage tube.

GB patent No. 2,106,784 disclosed another design in which a pressure sensitive adhesive layer is applied to the outside of the body portion on an adhesive releasing layer of silicone rubber so that the adhesive layer will be transferred from the outside of the body portion to its inside when rolling up the catheter to be delivered in a rolled-up condition. The manufacture of this catheter is laborious in that subsequent to the forming of the body portion by immersing a mandrel into a latex solution, it is necessary to effect rinsing and drying prior to the application of the silicone rubber layer. Then this layer must be further hardened before the application of adhesive which may be troublesome due to poor adherence to the surface of the silicone rubber layer.

SUMMARY OF THE INVENTION

An object of the present invention is therefore to provide an external catheter which reduces the possibility of leakage.

Another object of the present invention is to provide an external catheter that is more comfortable to the patient.

A further object of the invention is to provide a simplified eternal catheter.

The present invention achieves the foregoing objectives by providing an external catheter characterized in that the adhesive comprises a pressure sensitive adhesive. Also, before use, the catheter is delivered with the body portion rolled up from the open end towards the end at the drainage tube. At least a part of the outside of the body portion which is opposite the adhesive is provided with a cover layer having an adhesive rejecting surface.

As a result of the combination of an adhesive on the inside of the body portion and the cover layer on the outside, the catheter can be mounted safely and free of leakage when unrolling it from the rolled-up condition in which it is delivered. As no transfer of adhesive is taking place from one surface to another, difficulties are eliminated when unrolling and thus also the risk thereby involved of damaging due to too strong adhesion to the outside or to insufficient adhesive adherence to the inside, and the production of the catheter provides for a good adhesive adherence to the inside.

In the rolled-up condition the cover layer on the outside ensures that neighboring windings will not stick together throughout the length where the adhesive is applied.

As a result of the improved adherence, it is not necessary to apply the adhesive throughout the length of the body portion. A fully sufficient adherence for safe fastening is obtained by a preferred embodiment in which the adhesive layer and the cover layer extend across a strip-like zone on the inside and outside, respectively, of the body portion.

Contrary to the prior catheter according to the aforementioned GB patent, no different ability of adhesive adherence of the outside of the body portion is required, apart from the area provided with said cover layer, the body portion may be produced as a single-layer component of slight thickness, thereby increasing the convenience for the user.

The invention further relates to a method of manufacturing a catheter of the kind concerned, which is characterized by arranging a prefabricated catheter body portion around a substantially cylindrical mandrel which has previously been provided with a pressure sensitive adhesive, such that the adhesive on the mandrel contacts the inner surface of the body portion. A cover layer is provided such that the outer surface of the body portion is an adhesive rejecting surface. During subsequent rolling-up of the body portion, the inner surface of the body portion (now coated with adhesive) is rolled backward onto the adhesive-rejecting outer surface of the body portion. In preferred embodiments, a portion of the mandrel has an adhesive-rejecting surface to aid application of the adhesive to the inner surface of the body portion.

By this method, the manufacture is facilitated and the production costs reduced due to the fact that the body portion may be available as a prefabricated sheath and that adhesive may be easily applied in a desired, accurately measured amount with certainty of uniform results.

According to a preferred embodiment, the method may be carried out in that the adhesive layer is applied to the mandrel prior to the arrangement of the body portion by winding an adhesive rejecting zone on the mandrel with a prefabricated adhesive tape provided with adhesive on both sides. The adhesive applied to the side of the tape opposite the mandrel being a pressure sensitive adhesive.

It is thereby achieved that all components of the catheter, i.e., the body portion, the internal adhesive and the external cover layer, may be available as prefabricated components so that the use of components in a liquid state in the production is avoided. The use of a prefabricated adhesive tape allows a very accurate dosing of adhesive.

As a second possibility of a simplified production, the method may be carried out in that the adhesive is applied to a strip-like zone of the inside of the body portion mounted on the mandrel by applying the adhesive in a liquid state internally through the mandrel. For instance, adhesive may be supplied through adhesive supply ducts in the region of adhesive-rejecting surface of the mandrel.

The invention further relates to an apparatus adapted to carrying out the said method The apparatus comprises a rotatable, substantially cylindrical mandrel. In some embodiments, the mandrel may be provided with an annular circumferential depression having a width adapted to application of adhesive to the inner side of a mounted catheter body portion, or for receiving an annular insert having an outer adhesive-rejecting surface.

For carrying out the above mentioned preferred embodiment, an annular insert having an adhesive rejecting surface is disposed in the depression.

The above mentioned alternative embodiment of the method may also be carried out by means of an embodiment of the apparatus in which the mandrel is provided with adhesive supply ducts opening into the bottom of said depression.

BRIEF DESCRIPTION OF THE DRAWINGS

In the following, the invention will now be explained in more detail with reference to the drawings, in which.

DETAILED DESCRIPTION OF THE PREFERRED EMBODIMENTS

Figure 1:
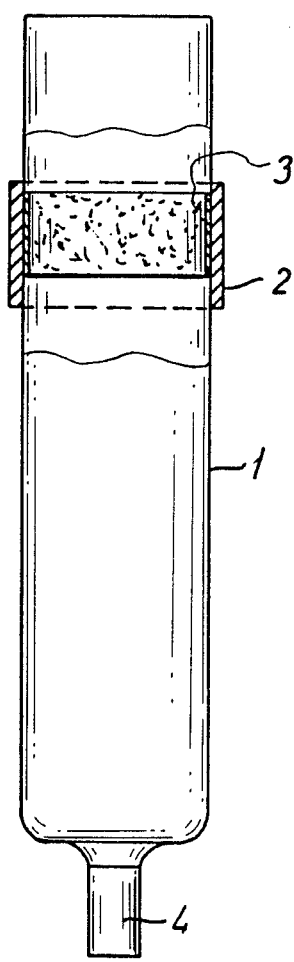
FIG. 1 is a longitudinal sectional view of an embodiment of a catheter according to the invention in its unrolled state of use.

In the embodiment of FIG. 1, the catheter comprises a substantially cylindrical body portion 1 having a diameter corresponding to a normal flaccid penis. The body portion 1 is manufactured as a soft, thin-walled single-layer component of an elastic material, preferably latex or synthetic rubber.

At one end, the body portion 1 merges into a narrowed drainage tube 4 for connecting the catheter with a urine collecting bag (not shown) through a hose that is likewise not shown. Such a collecting bag, may in a manner known per se, be adapted to be mounted for instance on one leg of the user.

At some distance from its open end the body portion 1 is, in the illustrated embodiment, provided with a strip-like adhesive layer 3 of a pressure sensitive adhesive, which may for instance be of the hydrocolloid-elastomeric type, so that the adhesive layer 3 is moisture-absorbing and will thus absorb perspiration moisture from the skin of the penis.

The adhesive layer 3 may be applied in such a thickness that it forms an elastically resilient ring ensuring fastening with good tightness and without any inconvenience to the user.

Opposite the adhesive layer 3 a likewise strip-like cover layer is applied to the outside of the body portion 1, said cover layer is applied to the outside of the body portion 1, said cover layer having according to the invention an adhesive rejecting surface. In the illustrated embodiment the cover layer 2 consists in a strip-like cover foil that may be applied to the body portion by means of an adhesive having a weaker adhesion so that the cover foil may possibly be detached after the catheter has been rolled on penis.

The adhesive rejecting surface of the cover foil may be obtained, for instance, by means of a surface coating of silicone rubber.

Figure 2:
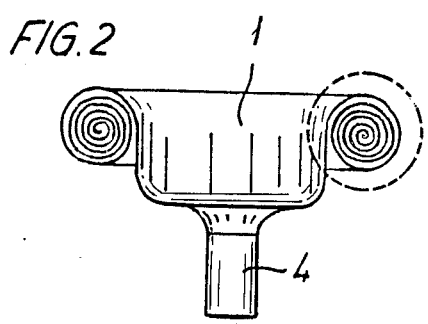
FIG. 2 is a longitudinal sectional view of the catheter in its rolled-up state of delivery.
Figure 3:
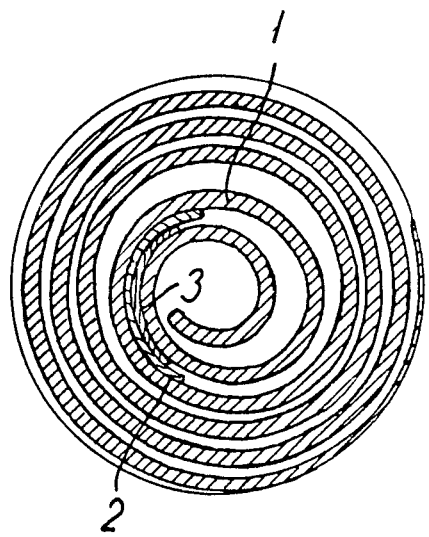
FIG. 3 is a detail of the portion of FIG. 2 in the circle, on a larger scale.

The described design entails that the catheter as illustrated in FIGS. 2 and 3 can be delivered in a rolled-up condition, thereby facilitating its arrangement. In the rolled-up condition the cover foil 2 will, as shown in the enlarged sectional illustration in FIG. 3, engage the adhesive layer 3 so as to prevent neighboring windings of the rolled-up catheter in the area of the adhesive layer 3 to stick to each other. In order to eliminate problems with cold-flowing of the adhesive the cover foil 2 has preferably a somewhat larger width than the adhesive layer 3.

Instead of the illustrated cover foil the cover layer 2 may consist of a strip-like covering of silicone rubber or other adhesive rejecting material applied by spraying, painting or the like.

The adhesive layer 3 may have any desired extension in the longitudinal direction of the catheter but, dependent on its thickness, the desired pliability and flexibility of the body portion 1 should be taken into consideration. There may possibly be more than one strip-like adhesive zone with an associated cover layer.

Figure 4:
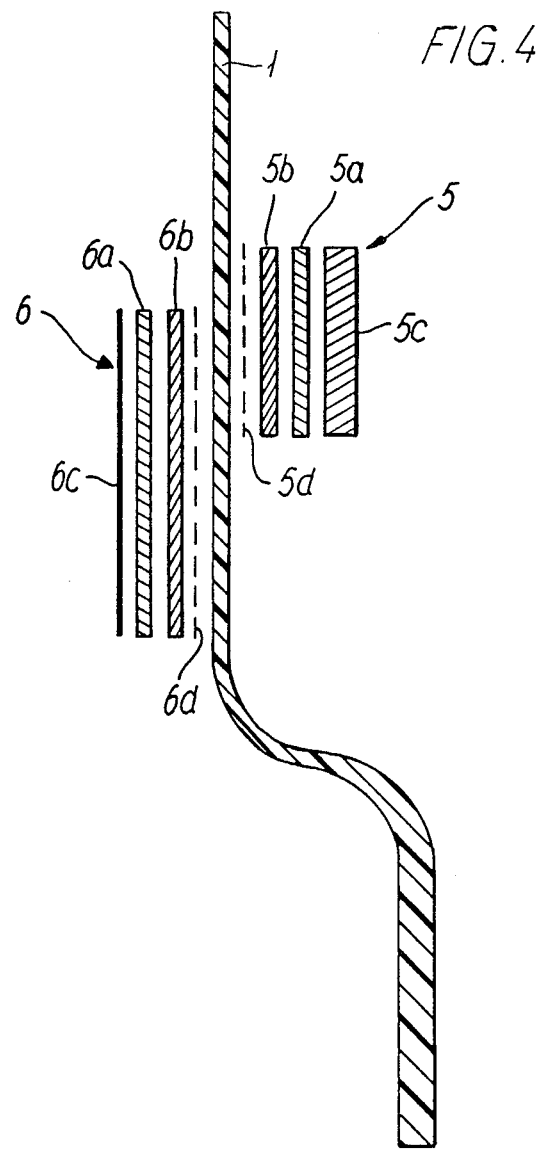
FIG. 4 is a schematical illustration of the design of an internal adhesive and an external cover layer in a preferred embodiment of the catheter.

As schematically illustrated in FIG. 4 the adhesive layer on the inner surface of the body portion 1 is according to a preferred embodiment manufactured in that an adhesive tape 5 is applied to the inner surface. In the illustrated embodiment the adhesive tape consists of a basic layer 5a of a plastic film of substantially smaller thickness than the body portion 1, e.g. a polyurethane film having a thickness of 5 to 25 mm, provided with an adhesive layer 5b of an adhesive having a good adhesion ability. For example, the adhesive can be an acrylic adhesive applied to that surface of the basic layer 5a which is adapted to be applied to the inner surface of the body portion 1. A layer 5c of the above mentioned pressure sensitive liquid absorbing adhesive is located on the opposite surface which is adapted to fasten the catheter to the penis. Such an adhesive tape may be prefabricated as a finished component for use in the production of the catheter and in this form it may be provided with a paper cover 5d above the adhesive layer 5d. The paper cover is torn off prior to mounting the adhesive tape 5 and the body portion 1 in mutual contact.

Similarly, a strip-like cover foil 6 to be mounted on the external surface of the body portion 1 may comprise a basic layer 6a of the same material and the same thickness as the basic layer 5a of the adhesive tape 5. On the surface of said basic layer 6a, which is adapted to be fastened to the body portion 1, there is provided an adhesive layer 6b of the same nature as the adhesive layer 5b. A thin layer 6c of an adhesive rejecting material, for instance silicone rubber, is applied to the opposite surface of the basic layer 6a. Also, the cover foil strip 6 may be prefabricated as a finished component and may in this condition be provided with a paper cover 6b above the adhesive layer 6b.

The composition illustrated in FIG. 4 of the adhesive tape 5 and the cover foil strip 6 allows production of the components from a common strip-like starting material comprising the elements 5a, 5b and 5d, 6a, 6b and 6d, respectively, which may subsequently be joined with the adhesive layer 5c and the adhesive rejecting surface coating 6c, respectively.

In FIG. 5 successive stages in a preferred method of manufacturing a catheter as illustrated in FIG. 4 are illustrated at A to D.

With the body portion 1, the adhesive strip 5 and the cover foil strip 6 as finished components the production is carried out on a rotatable, substantially cylindrical mandrel 7 whose free end is rounded substantially to a hemispherical shape.

In a zone in which the adhesive strip 5 is to be fastened the mandrel 7 is formed with a depression 8 accommodating an annular insert 9 of an adhesive rejecting material, for instance silicone rubber.

In the illustrated embodiment the mandrel 7 comprises a longitudinal duct 10 positioned substantially in the axis of rotation. The duct comprising outside the are of mounting the body portion 1 of a catheter, an attachment, not shown, for a hose or tube connection from a source of compressed air. Two inclined ducts 11 and 12 opening into a groove 13 at the upper surface of the hemispherical free end of the mandrel 7 are joined with the longitudinal duct 10. Further, two radial, diametrically opposite ducts 14, 15 likewise opening into annular grooves 16, 17 at the free surface of the mandrel are connected with the duct 10 on either side of the depression 8.

Figure 5A:
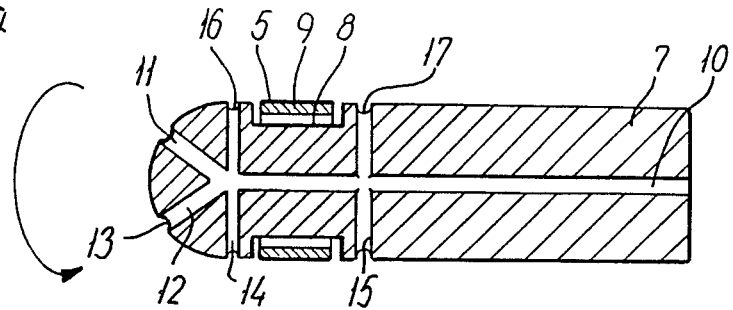
FIGS. 5a–5d illustrate successive stages of one preferred method of manufacturing a catheter in accordance with the invention using a first embodiment of an apparatus for such manufacture.
Figure 5B:
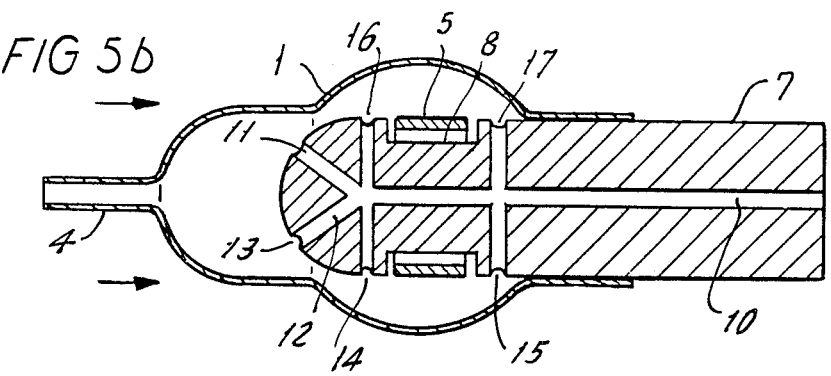

In the production of the catheter the adhesive strip 5 is first wound round the mandrel 7 on the insert 8 during rotation as shown in FIG. 5A. The body portion 1 is then arranged by supplying pressurized air through the ducts 10 to 12 and 14, 15 as illustrated in FIG. 5B, thereby inflating the body portion which may then be mounted in a correct position on the mandrel 7 without contact with the coating 5b of the adhesive strip. The paper cover 5d having been removed prior to winding on the mandrel 7.

By interruption of the supply of pressurized air the body portion 1 will be put into tight engagement against the surface of the mandrel 7 and the adhesive strip 5 wound thereon, thereby fastening the latter to the inside of the body portion 1.

Figure 5C:
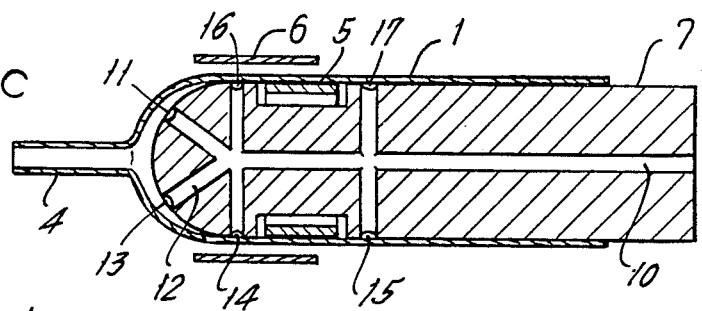
Figure 5D:
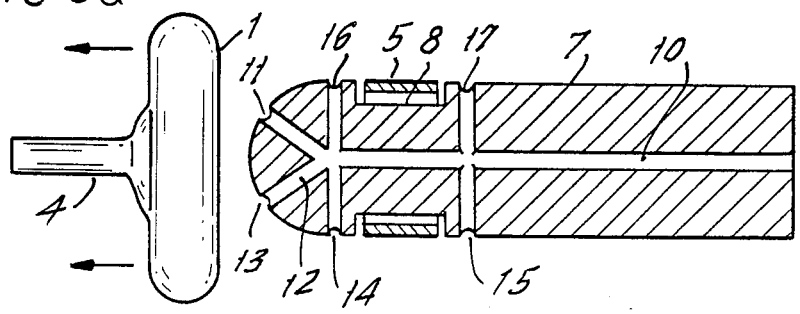

In this condition the cover foil strip 6 is mounted on the outside of the body portion 1 during rotation of the mandrel 7 and, as illustrated in FIG. 5c, at such a parallel displacement relative to the adhesive strip 5 that by the subsequent rolling-up of the body portion 1 to the condition shown in FIG. 3 it will become opposed to the adhesive strip 5 that by the subsequent rolling-up of the body portion 1 to the condition shown in FIG. 3 it will become opposed to the adhesive strip 5. The rolling-up is effected as illustrated in FIG. 5D while the body portion 1 still remains on the mandrel 7, and the finished catheter is thus ready for packaging.

The production of the catheter according to this method may be carried out on the basis of prefabricated components so that none of the components need be applied in a liquid state. Thus, no drying and hardening operations are involved and the time of production is shortened.

Figure 6:
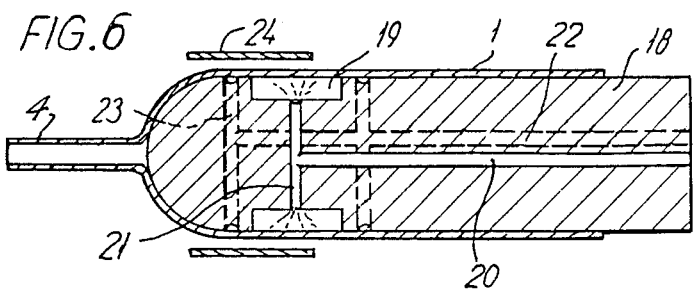
FIG. 6 is another embodiment of an apparatus for manufacturing a catheter in accordance with the invention.

FIG. 6 shows a mandrel 18 to be used in an alternative method. Also according to this embodiment the mandrel 18 is provided with a circumferential annular depression 19 in an area corresponding to the internal adhesive layer in the finished catheter. The application of adhesive is, however, effected by spraying liquefied adhesive through ducts 20, 21 opening into the bottom of the depression 19.

In order to control and locate the deposition of the sprayed adhesive, the mandrel 18 is further provided with suction channels 22, 23 through which a partial vacuum is provided by means of a suction device not shown, said vacuum keeping the body portion in tight engagement with the surface of the mandrel 18 so as to prevent flowing of the adhesive outside the depression 19.

In a similar manner the cover layer 24 is applied when liquefied which may be effected by spraying, painting or by means of a roller. According to this method of production the mandrel 18 is kept stationary during the period of the internal application of adhesive.

In this method the production of the catheter requires a certain time for drying and hardening before the rolling-up of the catheter can be effected.

Although the present invention has been described in connection with the preferred embodiments, many other variations and modifications will now become apparent to those skilled in the art without departing from the scope of the invention. It is preferred, therefore, that the present invention not be limited by the specific disclosure herein, but only by the appended claims.

What is claimed is:

1. A method for manufacturing an adhesive connecting external male catheter for urinary incontinence, which method comprises:
   (1) providing a substantially cylindrical mandrel having an adhesive-rejecting outer surface on at least a portion thereof;
   (2) applying an adhesive to said mandrel;
   (3) placing a prefabricated body portion of said catheter having an inner and outer surface around said mandrel such that said adhesive on said mandrel is bonded to said inner surface of said body portion;
   (4) applying, to at least a portion of said outer surface of said body portion a cover layer with an outwardly facing adhesive-rejecting surface;
   (5) rolling said body portion outwardly on itself wherein said body portion is removed from said mandrel and said adhesive remains on said body portion.

2. The method according to claim 1, wherein said pressure-sensitive adhesive is applied to said mandrel by winding a prefabricated adhesive tape having adhesive on both sides around said mandrel, the adhesive applied to a side of the tape in contact with said mandrel being a pressure-sensitive adhesive.

3. The method according to claim 2, wherein said body portion is mounted on said mandrel under inflation by controlled supply of pressurized air in an area around said adhesive tape.

4. The method according to claim 3, wherein said body portion is held to said mandrel by suction.

5. The method according to claim 1, wherein said cover layer is applied by winding a strip-like cover foil around said outer surface of said body portion while said body portion is positioned on said mandrel.

6. The method according to claim 1, wherein said cover layer is applied in a liquid state.

7. The method according to claim 1, wherein said adhesive is applied in a liquid state to said adhesive-rejecting surface of said mandrel.

8. The method according to claim 4, wherein said body portion is held to said mandrel by suction.

* * * * *